United States Patent [19]

Daicoff

[11] Patent Number: 5,074,869
[45] Date of Patent: Dec. 24, 1991

[54] VASCULAR OCCLUSION DEVICE

[76] Inventor: George R. Daicoff, 600 6th St. South, St. Petersburg, Fla. 33701

[21] Appl. No.: 540,863

[22] Filed: Jun. 20, 1990

Related U.S. Application Data

[63] Continuation of Ser. No. 248,953, Sep. 26, 1988, abandoned.

[51] Int. Cl.⁵ .............................................. A61B 17/12
[52] U.S. Cl. ..................................... 606/158; 606/202
[58] Field of Search ............... 606/157, 158, 202, 203; 600/31; 128/DIG. 25

[56] References Cited

U.S. PATENT DOCUMENTS

| | | | |
|---|---|---|---|
| 1,366,121 | 1/1921 | Dorsey | 128/327 |
| 1,827,241 | 10/1931 | Kempf | 128/327 |
| 2,045,750 | 6/1936 | Buschenfeldt | 606/202 |
| 2,455,859 | 12/1948 | Foley | 128/346 |
| 2,944,552 | 7/1960 | Cannon. | |
| 3,538,917 | 11/1970 | Salke. | |
| 3,635,223 | 1/1972 | Klieman. | |
| 3,831,583 | 8/1974 | Edmunds et al. | 128/346 X |
| 4,256,094 | 3/1981 | Kapp. | |
| 4,408,597 | 10/1983 | Tenney | 128/DIG. 25 X |
| 4,428,365 | 1/1984 | Hakky | 128/DIG. 25 X |
| 4,592,339 | 6/1986 | Kuzmak et al. | 606/157 X |
| 4,594,996 | 6/1986 | Ibrahim. | |
| 4,597,389 | 7/1986 | Ibrahim. | |
| 4,702,252 | 10/1987 | Brooks et al. | 128/344 |
| 4,708,140 | 11/1987 | Baron | 128/327 X |

OTHER PUBLICATIONS

"Intermittent Occlusion System", by Gerald W. Timm et al, IEEE Transactions on Biomedical Engineering, Oct. 1970 p. 352.

Primary Examiner—Michael H. Thaler
Attorney, Agent, or Firm—Bacon & Thomas

[57] ABSTRACT

A vascular occlusion device for blocking a blood vessel during surgery includes an elongated tube and a ring like structure which is adapted to fit over and around a blocked vessel. The ring like structure includes an annular balloon and a fabric sheath surrounding the balloon to protect it from overinflation. A stop cock and a syringe are operatively connected through the tube to the balloon so that the balloon can be controllably inflated by the syringe by use of the stop cock. And the degree of inflation can be maintained by closing the stop cock.

3 Claims, 1 Drawing Sheet

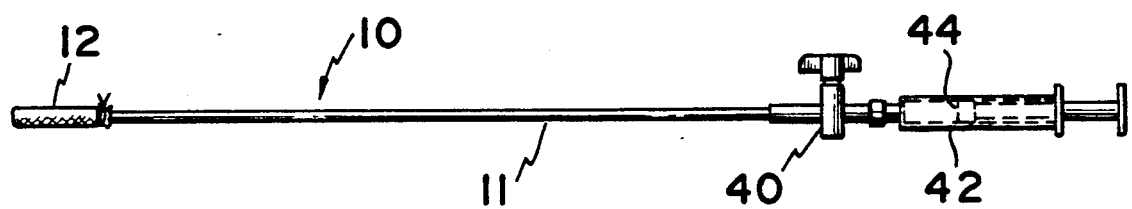
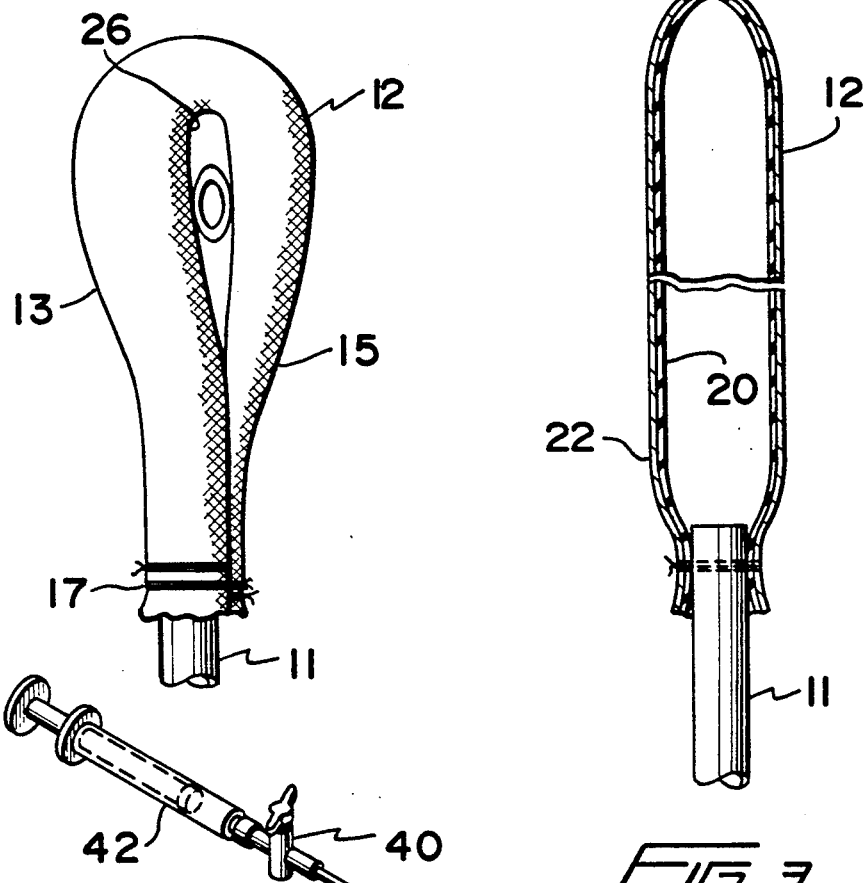

VASCULAR OCCLUSION DEVICE

This application is a continuation of application U.S. Ser. No. 07/248,953, filed Sept. 26, 1988 abandoned.

BACKGROUND OF THE INVENTION

This invention relates to a vascular occlusion device and more particularly to a balloon occlusion device for temporarily controlling the flow of blood through a graft or blood vessel in a human body.

New surgical techniques such as bypass of arterial stenoses or occlusions and replacement of segments of arteries involved by aneurysms or reconstruction following trauma, etc. involving the entire arterial tree has led to operation on more delicate and fragile vessels (e.g. coronary arteries, internal mammary arteries, saphenous veins) and therefore a need for a new, less traumatic, improved vascular occlusion device.

For example, in my copending U.S. patent application entitled "Implantable Graft Material and Method for its Fabrication" U.S. Ser. No. 07/235,510 filed Aug. 24, 1988, now abandoned I disclose a tubular graft which is suitable for blood vessel substitution such as those required for a variety of vascular procedures. However, such substitutions often require a temporary interruption in the flow of blood.

Vascular clamps of a variety of designs have been used to temporarily occlude blood vessels; however, they have been known to produce enough trauma to the vessel that disruption bleeding and early closure are known to have resulted from their use. This invention allows the least amount of pressure to occlude these vessels to stop blood flow and therefore is the least traumatic.

One approach to temporarily close the blood vessels providing arterial blood, without leaving the vessel more susceptible to thrombosis is disclosed in the U.S. Pat. No. 3,538,917 of Robert G. Selker. The Balloon Occlusion Clip disclosed therein is adapted to be positioned about the vessel for use in 2-4 mm vessels in intracranial surgery. An inflatable member is shaped to surround at least a portion of the vessel and upon inflation, occludes the vessel.

The occlusion clips overcome many of the disadvantages of metallic clips used in surgery. For example such clips may be used to completely occlude a vessel without damaging the internal lining of the vessel. However, such clips do not satisfy the needs required for many of today's vascular and cardiac surgical techniques. For example, they do not include means for maintaining a desired degree of occlusion, thus freeing the hands of the surgeon, are not adapted for positioning in a remote area without interfering with the surgical operation, and do not include means for preventing slippage along the vessel without damaging the vessel or actually slipping off the vessel. Applicant's device completely surrounds the vessel and is used in areas other than intracranial surgery.

A U.S. Patent of Adel A. Ibrahim U.S. Pat. No. 4,597,389 discloses a device for positioning a surgical balloon in a remote area of a human body. However, these devices are not adapted to pass over or around the conduit. They do not include means for preventing slippage along a vessel.

SUMMARY OF THE INVENTION

Briefly, a vascular occlusion device, according to the present invention includes an elongated tubular member and a ring like encircling element attached to the distal end of the tubular member. The encircling element has an open ring like structure and is adapted to pass over and into surrounding engagement with a vascular conduit such as a vein or artery of a patient. The encircling element includes a balloon and a fabric sheath surrounding the balloon and protecting the balloon from overdistension. The encircling element includes one free end and fastening means such as a ligature for securing the vascular conduit around the blood conduit. Where a free end vessel is to be occluded the encircling element is already closed inflating means such as a syringe is operatively connected or attached to the proximal end of the tubular member for inflating the balloon to thereby occlude the vascular conduit to a desired degree. The vascular occlusion device according to the present invention also includes valve means such as a stop cock for maintaining the degree of inflation of the balloon, so that the vascular conduit can be occluded and maintained at a desired degree of occlusion with a minimum amount of trauma to the vessel or graft.

The vascular occlusion device according to the present invention overcome a number of shortcomings in the prior art. For example, the devices can be readily positioned in relatively remote areas of the body in a manner which does not interfere with the surgeon. In addition, the device can be used to completely or partially occlude a vessel to the degree desired without causing undue damage to vessel or artery an without undue trauma to the patent.

The devices according to the present invention also include means for maintaining a desired degree of occlusion thus freeing the hands of the surgeon or surgical assistant for other tasks. And, if desired the degree of occlusion may be readily increased or reduced in a controlled manner without interfering with the chief surgeon. In addition, the devices according to the present invention include means to reduce the likelihood of undesirable slippage along the vessel or artery. The device can also be produced at a relatively low cost and will normally be discarded after a single use.

These and other advantages of the invention will become apparent from the following detailed description taken together with the accompanying drawings.

BRIEF DESCRIPTION OF THE DRAWINGS

FIG. 1 is a side elevational view of a vascular occlusion device according to a preferred embodiment of the present invention;

FIG. 2 is a cross-section showing the court reactions of the distal portion of the vascular occlusion device of FIGS. 1;

FIG. 3 is a side elevational view of the distal portion of FIG. 2 illustrating the distal portion of the vascular occlusion device surrounding an artery; and FIG. 4 is a perspective view showing the vascular occlusion device and a vein which is compressed clearly.

DETAILED DESCRIPTION OF THE INVENTION

In the drawings, like elements are presented by like numerals throughout the several views.

Referring now to FIG. 1, a vascular occlusion device 10 includes a semirigid elongated hollow tubular member or tube 11 and an encircling element 12 which is attached to the distal end of tube 11.

The encircling element 12 is shown more clearly in FIGS. 2 and 3. As illustrated therein, the encircling element 12 is formed essentially of an elongated closable portion 13 which is adapted to slip over or around a patents vein or artery 14. The portion 13 also includes an extension 15 which is adapted to close the double portion 13. For example, the extension 15 may be a simple suture 17 to be tied to the tube 11 or may comprise a fabric flap of polyester material or the like which is used to close the open portion 13 after it is passed over a vein or artery 14. Fastening means such as a hook and eye (not shown) may be fastened to the portion 13 and extension 15.

The encircling element 12 can thus be readily passed over and around a blood vessel or artery 14 and the element closed by fastening a snap fastener on to a post or the like or closed by tying the suture 17 to tube 11. For an open end vessel: The encircling element 12 will be pre-tied and closed.

The encircling element 12 includes an annular inflatable balloon 20 and a fabric sheath or envelope 22 which surrounds the balloon 20. The outside circumference 24 of the fabric sheath 22 is fixed and prevents the balloon from expanding outwardly, while an inner portion 26 of the sheath 22 has sufficient slack to permit the balloon to inflate inwardly in a radial direction. However, the sheath 22 permits only limited inflation and thereby prevents overdistension of balloon 20 while allowing complete occlusion of the vein or artery 14.

In the preferred embodiment, the sheath or envelope 22 is made of polyester or other fabric that can be readily sterilized or is suitable for surgical use as will be readily understood by those who are skilled in the art. The balloon 20 can be fabricated of silicone elastomer, latex, or the like.

It has also been found desirable to provide a textured or fabric surface 28 for engaging the vein or artery 14. For example, a fabric surface such as one provided by a relatively course fabric reduces the tendency of the encircling element 12 to slip along the artery 14. In effect the fabric provides a soft gripping surface when the balloon 20 is further extended without causing trauma to the patient.

A fabric as described above can be made of 70 denier polyester or polyethylene terephthalate fiber using a knitting machine with a 16 needle head in a manner which will be readily understood by those who are skilled in the textile arts.

The semirigid tube 11 may be made of any suitable plastic material such as polyethelene, polypropylene or the like and should have a reasonable degree of flexibility. For example, this semirigid tube 11 is used to direct the encircling element 12 along a vein or artery 14 so that the flow of blood through the vein or artery 14 may be occluded or restricted at an optimal location.

A stop cock or valve 40 and syringe 42 are operatively connected to tube 11 at the proximal end thereof. For example, the syringe 42 can be threadedly connected to one end of stop cock 40 and connected through the stop cock 40 (when in its open position) to the tube 11 and when the stop cock is in an open position, the balloon 20 can be inflated by depressing plunger 44.

The operation of the vascular occlusion device 10 involves slipping the open portion of the element 12 over a vein or artery as described above. The extension 15 of the encircling element 12 is then fastened by means of the suture or stitch 17 to a portion of the element 12 to thereby close the ring in surrounding engagement with the vein 14. Actually, the encircling element fits loosely over the vein as long as the balloon 20 is in its collapsed or uninflated condition.

The encircling element 12 is then forced along the vein 14 by means of tube 11 or with the assistance of the surgeon's fingers until it is in an optimal position for occlusion of the vein or artery 14. The surgeon or surgical assistant then opens the stop cock 40 and depresses the plunger 44 in syringe 42 to thereby inflate the balloon 20 and obstruct the vein or artery 14 to the desired degree. The surgeon or surgical assistant then closes the stop cock 40 to maintain the selected degree of occlusion.

Then when the surgical procedure is completed, the stop cock 40 can be opened slowly and the initial flow of blood controlled by means of the plunger 44. And, when the surgeon is satisfied with the patient's condition the encircling member can be opened for removal but will in most case be cut to thereby free the vein from the device.

While the invention has been described with respect to certain embodiments, it will be obvious that various modifications may be made by those skilled in the art without departing from the scope of the invention as defined by the claims.

What is claimed is:

1. A vascular occlusion device for use by a surgeon during vascular surgery comprising the combination of an elongated semi-rigid tubular member and an encircling element attached to the distal end of said semi-rigid tubular member for passing over and into surrounding engagement with only a singular vascular conduit of a patient, means including said elongated semi-rigid tubular member for positioning said encircling element in a remote area along the singular vascular conduit, said encircling element including an annular balloon and a fabric sheath surrounding said balloon for preventing said balloon from expanding outwardly but having sufficient slack to permit said balloon to inflate in an inwardly radial direction to thereby prevent overdistension of said balloon while allowing complete occlusion of the singular vascular conduit and said fabric sheath having a soft but coarse gripping inner surface for engaging a singular vascular conduit and providing resistance to slippage along the vascular conduit, fastening means attached to said encircling element to secure said encircling element around the vascular conduit, a syringe operatively connected to the proximal end of said tubular member for inflating said balloon through said tubular member to thereby occlude the vascular conduit to a desired degree, and a stop cock for maintaining the degree of inflation of said balloon separating said syringe and said balloon and disposed adjacent said syringe and connected thereto at the proximal end of said tubular member whereby the vascular conduit can be occluded and maintained at the desired degree of occlusion with a minimal amount of trauma to a patient.

2. A vascular occlusion device according to claim 1 wherein said encircling element is adapted to expand inwardly in a radial direction, said fabric sheath is polyethylene terephthalate and said annular balloon is made of silicone elastomer.

3. A vascular occlusion device according to claim 2 in which said elongated tubular member is made of polyethylene.

* * * * *